(12) United States Patent
Witt-Enderby et al.

(10) Patent No.: US 8,535,706 B2
(45) Date of Patent: Sep. 17, 2013

(54) BONE IMPLANT (75) Inventors: Paula A. Witt-Enderby, Bethel Park, PA (US); Kenneth McGowan, Harrison City, PA (US); James Rutkowski, Clarion, PA (US); Ellen S. Gawalt, Pittsburgh, PA (US); Rachelle Palchesko, Lucerne Mines, PA (US)

(73) Assignees: Duquesne University of the Holy Spirit, Pittsburgh, PA (US); Kenneth A. McGowan, Allegheny County, PA (US)

( * ) Notice: Subject to any disclaimer, the term of this patent is extended or adjusted under 35 U.S.C. 154(b) by 0 days.

(21) Appl. No.: 13/521,361

(22) PCT Filed: Jan. 10, 2011

(86) PCT No.: PCT/US2011/000039
§ 371 (c)(1),
(2), (4) Date: Jul. 12, 2012

(87) PCT Pub. No.: WO2011/084898
PCT Pub. Date: Jul. 14, 2011

(65) Prior Publication Data
US 2013/0029960 A1  Jan. 31, 2013

Related U.S. Application Data (60) Provisional application No. 61/335,723, filed on Jan. 11, 2010.

(51) Int. Cl.
*A61F 2/28* (2006.01)

(52) U.S. Cl.
USPC .................................................. 424/426

(58) Field of Classification Search
None
See application file for complete search history.

(56) References Cited

U.S. PATENT DOCUMENTS 8,323,348 B2 * 12/2012 Lai et al. ............... 623/23.5
2005/0260753 A1  11/2005 Shahar et al.
2007/0224678 A1  9/2007 McGowan et al.

OTHER PUBLICATIONS

Jose Luis Calvo-Guirado et al., "Melatonin plus porcine bone on discrete calcium deposit implant surface stimulates osteointegration in dental implants," Journal of Pineal Research, 2009, vol. 47, No. 2, pp. 164-172.
M. Takechi et al., "Effect of FGF-2 and melatonin on implant bone healing: a histomorphometric study," Journal of Materials Science: Materials in Medicine, 2008, vol. 19, No. 8, pp. 2949-2952.

* cited by examiner

*Primary Examiner* — Carlos Azpuru
(74) *Attorney, Agent, or Firm* — Barbara E. Johnson, Esq.

(57) ABSTRACT

A bone implant, and bone implant material, includes a calcium- and oxide-containing artificial graft material in a scaffold, to which melatonin and an optional cell adhesion peptide are absorbed or covalently linked.

3 Claims, 7 Drawing Sheets

FIG. 1

|  | All$_{auto}$ | All$_{120}$ | A/B$_{650}$ | C$_{650}$ | A/B$_{room}$ | C$_{room}$ |
|---|---|---|---|---|---|---|
| CaAl$_2$O$_4$ | X | X | X | X | X | X |
| CaAl$_4$O$_7$ | X | X |  | X | X | X |
| CaAl$_2$((OH)$_8$(H$_2$O)$_2$)(H$_2$O)$_{1.84}$ |  |  |  |  | X | X |
| Al(OH)$_3$ | X | X | X |  | X | X |
| CA$_3$Al$_2$(OH)$_{12}$ |  |  |  |  | X |  |
| 3CaO-Al$_2$O$_3$-Ca(OH)$_2$-18H$_2$O |  |  | X |  |  | X |
| 5(CaO)$_3$Al$_2$O$_3$ |  | X |  |  |  |  |
| (CAO)$_3$Al$_2$O$_3$(H$_2$O)$_6$ |  |  |  |  |  |  |
| Ca$_3$(Al(OH)$_6$)$_2$ | X |  |  |  |  |  |

- All mixtures include CaAl$_2$O$_4$ and CaAl$_4$O$_7$, which are the phases present in the unhydrated starting aggregates.
- The "X" indicates the phase list is present in that particular mixture.

Linker deposition: 12 aminododecanoic acid at room temperature

Maleimide Coupling: 3-maleimidopropionic acid NHS ester (ACN)

Michael addition: KRSRC or RGDC in refrigerated solution

| Mixture | -10+30 | -30+60 | -60 | -325 | AvgPore Diameter |
|---------|--------|--------|------|------|------------------|
| A | - | 25% | 25% | 50% | 100μm |
| B | 25% | 25% | 25% | 25% | 150μm |
| C | 33% | 33% | 34% | - | 200μm |
| D | 50% | 50% | - | - | 260μm |
| E | 100% | - | - | - | 290μm |

BONE IMPLANT

This application claims the benefit of U.S. Provisional Patent Application Ser. No. 61/335,723, filed 11 Jan. 2010, which is incorporated herein by reference.

BACKGROUND OF THE INVENTION

1. Field of the Invention

The invention pertains to bone grafting material, bone graft articles and compositions, and methods of enhancing healing or desired tissue growth by adding Melatonin to bone grafts, implants, and tissue engineering scaffolds.

2. Description of Related Art

Melatonin is a well known hormone, best known to lay persons and others as an over-the-counter oral supplement useful in combating jet lag and insomnia. Melatonin, chemically known as N-acetyl-5-methoxytryptamine, is a naturally-occurring compound found in animals, plants, and various microorganisms. In humans and animals, Melatonin production and circulating blood levels vary, and govern, a number of biological functions in a daily circadian rhythm including but not limited to sleep cycles. While much is known about Melatonin, it is most often thought of even among health care providers as a circadian regulator, an anti-oxidant, and for suspected efficacy in (without limitation): cancer prevention and treatment; prevention or treatment of ischemic or cardiovascular disease; treatment of Attention Deficit Hyperactivity Disorder; reduction of incidence of infertility; reduction of occurrence or severity of headaches; treatment of mood disorders, reduction of gall bladder stones, and treatment of Amyotrophic Lateral Sclerosis.

Prior to the present invention discussed below, minimal if any attention has been given to the ability of in situ Melatonin to enhance bone healing in a bone implant or graft scenario, or to enhance tissue growth on a tissue engineering scaffold. Instead, bone healing has heretofore been a medical art in which various materials and substances have been used to enhance bone healing with or without bone grafts of various types, as described below.

There are approximately 500,000 joint replacement and bone graft surgeries annually in the United States and 2.2 million bone surgeries annually worldwide, making bone the second most commonly transplanted tissue (skin is the first most commonly transplanted tissue). The two most common methods of bone replacement are the autograft and the allograft, which together make up about 90% of the bone grafts used overall. Autologous bone grafts (autografts) involve selecting and moving a portion of a patient's own bone to serve as a bone graft, such as in patients requiring extensive jaw reconstruction whose jaw bones are grafted from bone shavings taken from the patients' own hip bone. Allografts may be made from exogenous human bone—generally cadaverous bone from a bone bank rather than bone donated from a donor, and xenografts (such as bovine bone) are typically highly engineered before use and are often distributed as simple calcified matrices.

The use of synthetic materials rather than human or animal based grafts can eliminate disease transmission and provide larger implants or scaffolds than is otherwise feasible. Artificial or synthetic bone graft materials include without limitation metal replacements, ceramics such as calcium phosphates (e.g. hydroxyapatite and tricalcium phosphate), BioGlass® brand of bioactive glass containing $SiO_2$, $Na_2O$, CaO and $P_2O_5$, and those based on calcium sulfate, all of which are biologically active to different degrees depending on their individual solubilities in the physiological environment. Synthetic scaffolds and bone graft materials in recent times have made up only about 10% of all bone graft materials used. Synthetic scaffolds strive to meet several criteria: osteo-conductivity; osteoinductivity; osteogenicity; and good osteointegration. Challenges in meeting these criteria center around the need for materials which are strong but not brittle while being nonetheless adequately porous to allow solid integration of the adjacent growing and healing bone.

Most bone graft materials may be crafted as a solid construct for insertion, or as a powder for pouring, into bone voids or bone wounds of many kinds. Such voids or wounds include, without limitation, dramatic reconstructions such as those that are needed in combat situations, as well as everyday bone voids that occur in mandibular or maxillary bone after tooth extractions. Comparatively recently, calcium aluminate based bone graft and implant materials have attracted increasing attention in bone repair and healing.

A prior art published patent application of interest is U.S. Published Patent Application No. 20070224678, entitled "Functionalized Artificial Bone and Joint Compositions and Methods of Use and Manufacture," published on Sep. 27, 2007. In this Published Patent Application (hereinafter "678"), the specification identifies certain functionalizations of calcium aluminate compositions by affixing a linking agent thereto, which linking agent is then used to link a biologically active agent such as an antibiotic (ampicillin for example), a peptide, or other active agent to the calcium aluminate substrate surface.

From a commercial standpoint, artificial or synthetic bone graft materials are arguably preferable to auto-, allo- and xeno-graft materials. However, some prior art artificial bone graft materials, such as calcium phosphate based materials, are excessively brittle to permit good results, because the three-dimensional scaffolds made from these brittle materials cannot avoid cracking or breaking upon implantation. Other synthetic bone graft materials, such as the calcium aluminate based compositions, both unhydrated and hydrated, are not excessively brittle and can provide a much better bone graft and bone implant scaffold than certain other ceramic or glass materials. Heretofore both calcium- and non-calcium based materials, including titanium and stainless steel bone replacement joints, have often been plagued by unwanted effects such as formation of excessive scar tissue adjacent to an implant. Scar tissue formation adjacent an implanted surface interferes with the interface between the implant and the bone and prevents the ultimate successful joining of bone to implant or graft. Indeed, some hip replacement surgeries result in the formation of so much scar tissue between the new joint and the adjacent bone that the surgery must actually be repeated to remove and replace the implant(s) altogether. Even the acknowledged very good artificial bone compositions according to U.S. Published Patent Application No. 20070224678 can allow an unacceptable amount of scar tissue to form adjacent the materials in vivo, with fibroblast formation being indicative of, and the predominant substituent of, this unwanted scar tissue. A need thus remains for a vastly improved bone graft, bone implant scaffold and healing enhancement material, able to accomplish all of: a) greatly improved bone wound healing; b) suppression of fibroblast growth and scar tissue formation; and c) good physical property characteristics for grafting or implantation (strength without brittleness). In addition, ideally such a material will be able to be formed or molded at room temperature with simple equipment, to enhance bone grafting and wound healing in the most difficult surgical environments of combat or disaster response areas as well as in everyday hospital procedures.

SUMMARY OF THE INVENTION

In order to meet this need, the present invention is the combined use—whether by adsorption or covalent linkage—of Melatonin adjacent any bone implant or graft, preferably any calcium- and oxide-containing artificial bone graft material, and more preferably a calcium aluminate composition. Even more preferably, the calcium aluminate composition—either as a solid or as a powder—is functionalized with Melatonin via a covalent bond faciliated by an intermediate chemical linkage (linker molecule). When Melatonin is introduced adjacent a calcium- and oxide-containing artificial bone graft material (either by coadministration with, adsorption to or linkage to the calcium- and oxide-containing substrate), surprisingly not only is bone healing greatly accelerated but the formation of fibroblasts in the area is actually suppressed while still increasing osteoblast formation, which for the first time known to the inventors gives a bone graft material that both dramatically speeds up bone healing and simultaneously reduces adjacent scar tissue formation in the area of the bone implant or graft.

DETAILED DESCRIPTION OF THE INVENTION

The present invention is the combined use—whether by adsorption or covalent linkage—of Melatonin adjacent any bone implant or graft, preferably any calcium- and oxide-containing artificial bone graft material, and more preferably a calcium aluminate composition. Even more preferably, the calcium aluminate composition—either as a solid or as a powder—is functionalized with Melatonin via a covalent bond facilitated by an intermediate chemical linkage (linker molecule). When Melatonin is introduced adjacent a calcium- and oxide-containing artificial bone graft material (either by coadministration with, adsorption to or linkage to the calcium- and oxide-containing substrate), surprisingly not only is bone healing greatly accelerated but the formation of fibroblasts in the area is actually suppressed while still increasing osteoblast formation, which for the first time known to the inventors gives a bone graft material that both dramatically speeds up bone healing and simultaneously reduces adjacent scar tissue formation in the area of the bone implant or graft.

In the practice of the invention, the coadministration, adsorption or linking of Melatonin to the bone graft substrate preferably involves Melatonin per se, although the use of the precursors or metabolites of Melatonin (including but not limited to 5-hydroxytryptophan (5OHTrp), 5-hydroxytryptamine (5HT), N-acetyl-5-hydroxytryptamine (NA5OHT) or 6-hydroxymelatonin (6OHMEL)) still falls within the scope of this invention albeit in a less preferred way. Interestingly, a substrate having Melatonin adsorbed or linked thereto may be autoclaved, such as at 180° C., with the Melatonin's surviving the autoclaving process intact. However, Melatonin cannot survive the much higher sintering temperatures used to make certain bone grafts and implants, so that if Melatonin is used with bone graft or scaffold materials that must be sintered, the Melatonin must be adsorbed or chemically linked thereto after sintering.

When calcium- and oxide-containing substrates are used for coadministration, adsorption or linking of Melatonin according to the present invention, the pore sizes in the powders, constructs or scaffolds should be in the range of 60-200 µm, preferably 80-180 µm and most preferably 100-150 µm, and the particle sizes of pourable, castable or moldable powders containing these pore sizes should be on the order of 300-1500 µm. Pourable, castable or moldable powders may be mixed with water or other reactive or unreactive liquid carrier(s) and used to form a structure when the materials set or cure, especially (as discussed elsewhere herein) when the calcium- and oxide-containing substrate is internally hydrated and thus has enhanced internal ability to set or cure upon wetting.

When Melatonin is coadministered or adsorbed to a bone graft material, the amount of Melatonin present should be on the order of about one-twentieth to one-sixtieth of a milligram of Melatonin per square millimeter of bone graft or implant material surface area with a rough calculation of about 0.006 milligram per square millimeter. Likewise, when Melatonin is linked to a bone graft or implant material, the amount of Melatonin present should be on the order of about one twentieth to one-sixtieth of a milligram of Melatonin per square millimeter of bone graft or implant material surface area, with a rough calculation of about 0.006 milligram per square millimeter. By "rough calculation" is meant that empiric testing cannot determine the exact amount of Melatonin linked or adsorbed to a substrate according to the invention, but by calculation and estimation of depletion of dipping fluids or linking constituents it is possible to determine the above quantification of the presence of Melatonin (or its precursors or metabolites).

Figure 2:
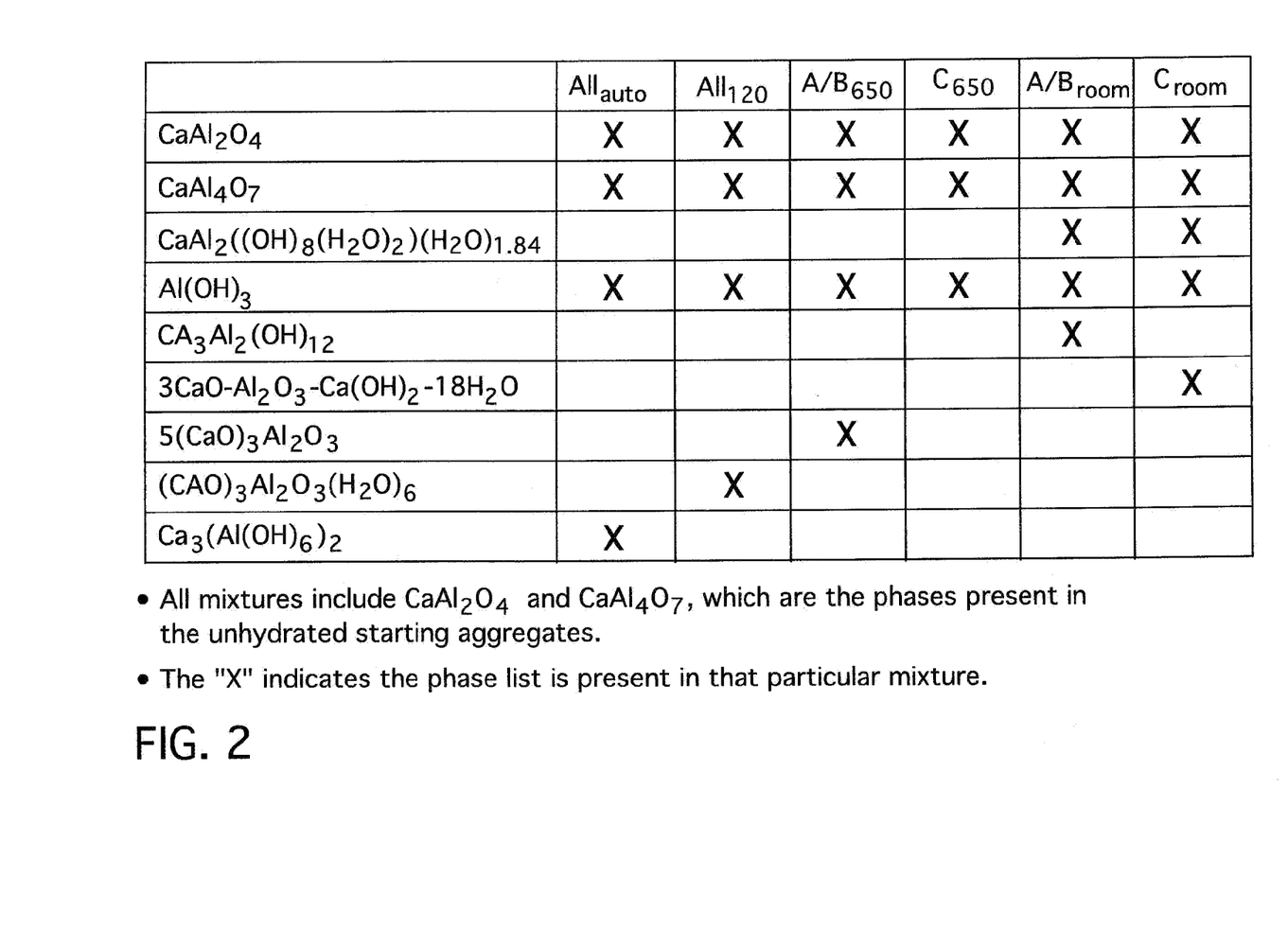
FIG. 2 is a table showing the Phases Present in Cast CA (calcium aluminate), illustrating in pertinent part that three of the five phases are shared in common among autoclaved CA versus CA formed at room temperature.

When calcium aluminate compositions are used according to the invention, they may be prepared as set forth in Example 1 below. Also, the calcium aluminate compositions of U.S. Published Patent Application No. 20070224678, which is hereby incorporated herein by reference, may be used without limitation in the practice of the present invention. Porous calcium aluminate containing substrates of the present invention are very strong, and generally have a modulus of rupture of about 1030 psi and a cold crushing strength of about 8630 psi. The porous calcium aluminate containing substrates according to the invention should have pore sizes in the range of 60-200 µm, preferably 80-180 µm and most preferably 100-150 µm. Materials of these porosities may be made by casting commensurately sized particulates and such casting methods are within the ordinary skill of the art (see also Example 1 below). Heat treatment of calcium aluminate materials generally does not affect pore size unless the heat treatment starts to exceed about 1600° F. However, heat treatment of hydrated calcium aluminate materials will increase porosity (due to the water molecule's leaving) starting at around 350° F. Phases present in "Cast CA" (cast calcium aluminate) are shown in FIG. 2.

Figure 1:
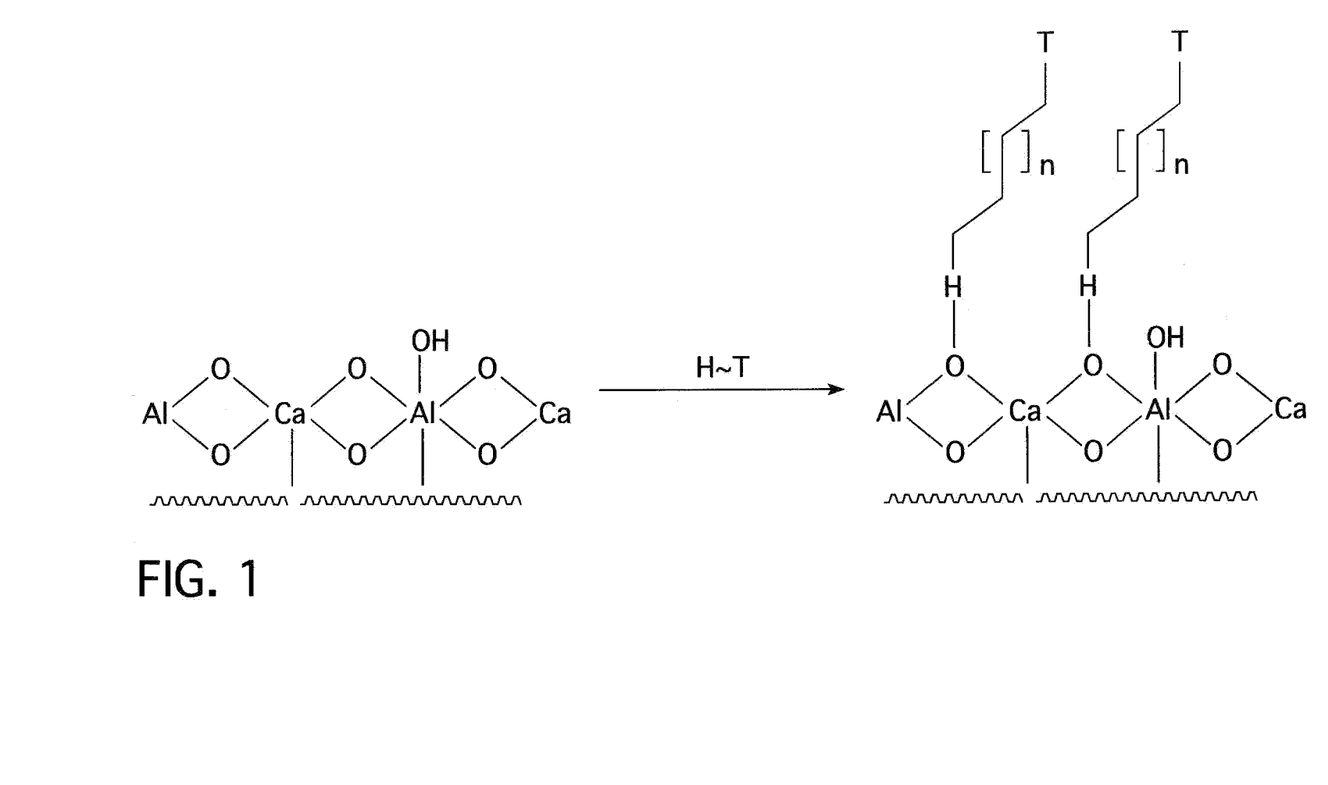
FIG. 1 is a schematic showing the basic H-T arrangement of a linker molecule between a bone implant or graft substrate and the Melatonin or peptide substituent appended from the T end of the linker.
Figure 3:
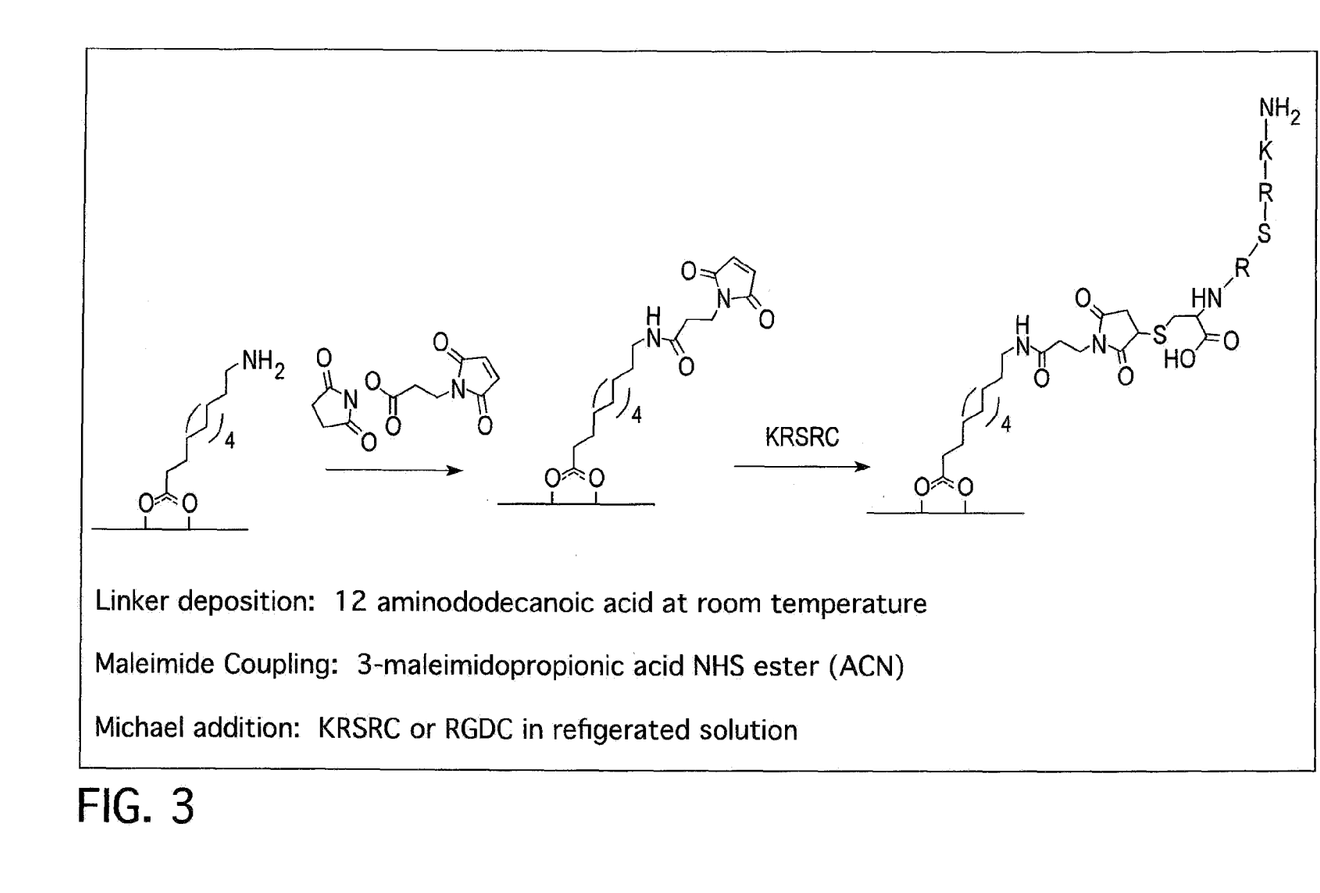
FIG. 3 is a chemical formula showing an exemplary regimen on a particular linker deposition, maleimide coupling, and Michael addition.
Figure 4:
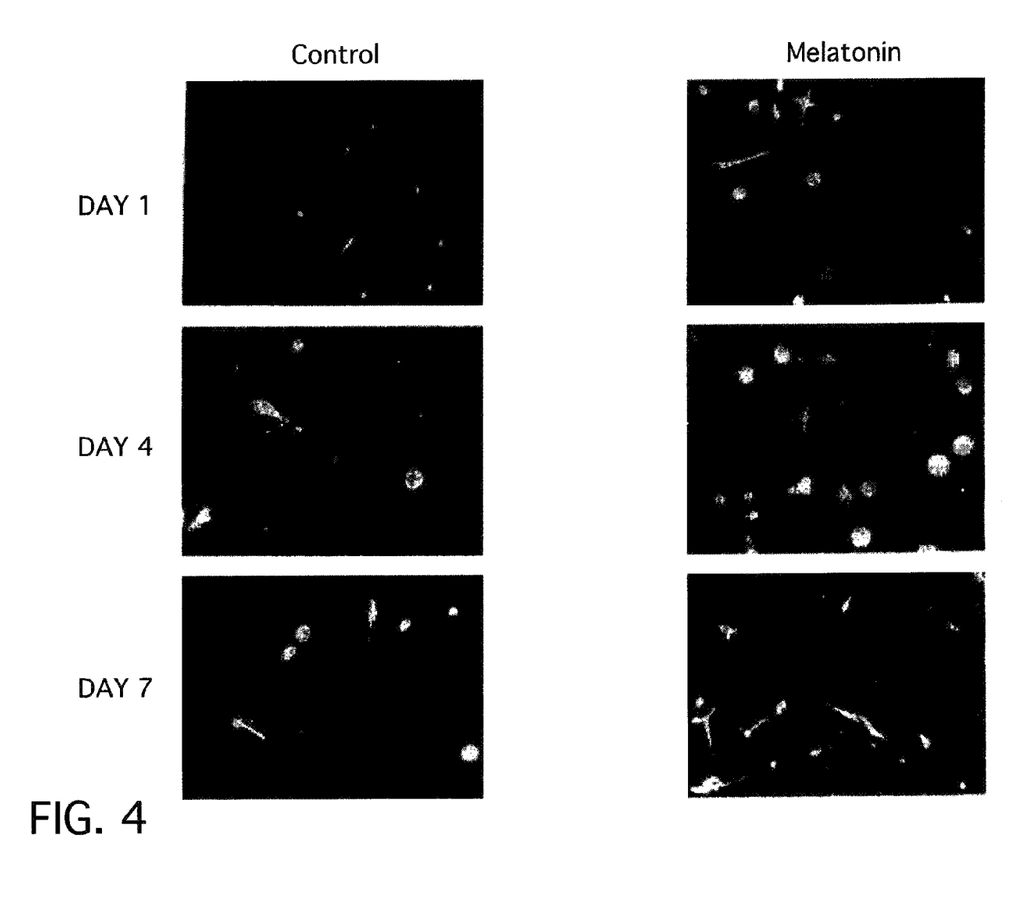
FIG. 4 shows photographs of CA with and without the Melatonin of the present invention, and osteoblast growth at days 1, 4 and 7.
Figure 5:
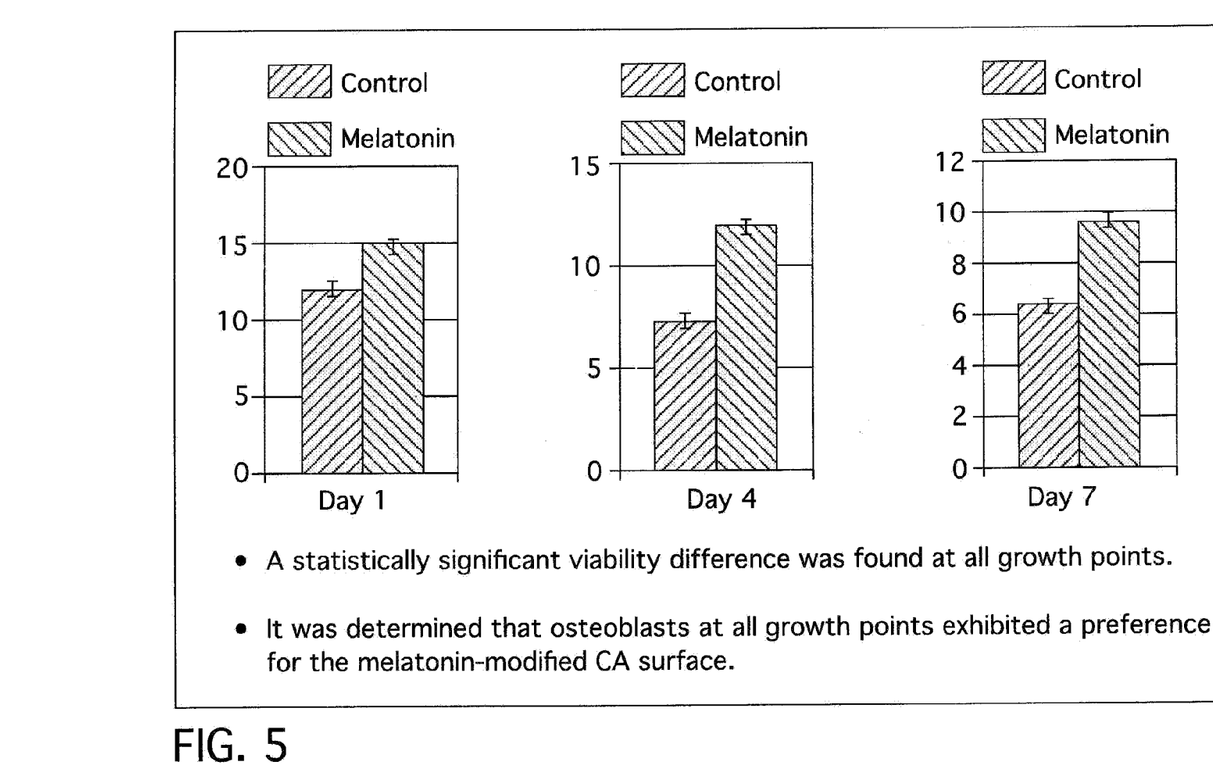
FIG. 5 is a set of three bar graphs representing "Osteoblast Statistics on Melatonin-Modified CA."
Figure 6:
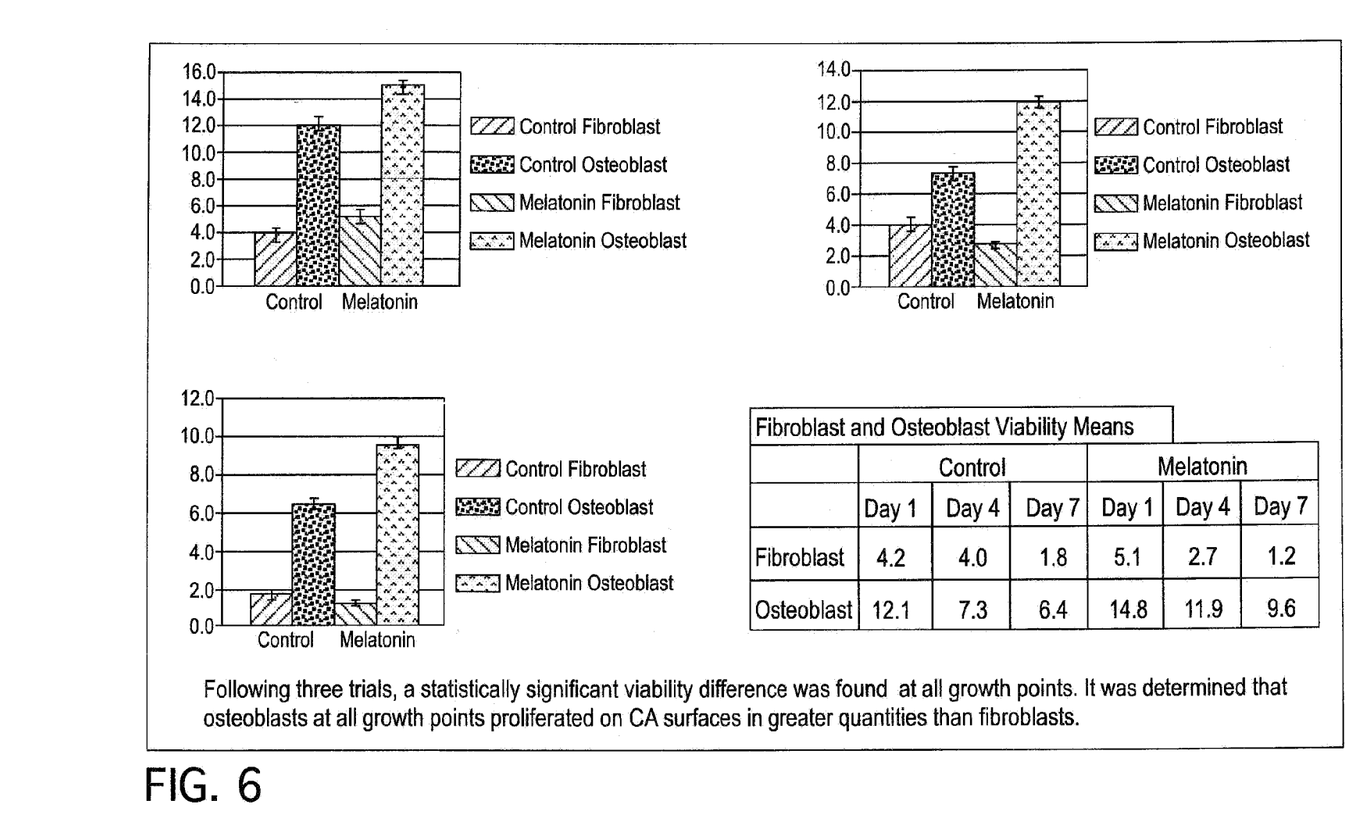
FIG. 6 is a set of three bar graphs entitled, "Cell Type Comparison," showing data which establish that Melatonin-modified CA both reduces fibroblast formation and increases osteoblast proliferation.

The chemical linkage of Melatonin to the calcium aluminate compositions may be accomplished in various ways. FIG. 1 illustrates the basic H/T arrangement of a linker molecule between a bone implant or graft substrate and the Melatonin or peptide substituent (not shown) appended from the T end of the linker. The reactive oxides on the surface of the metal oxide, calcium- and oxide-containing substrate or other oxide-containing substrate typically allow for covalent bonding of virtually any protonated or deprotonated organic acid moeity, including but not limited to carboxylic, sulfonic, phosphonic or hydroxyamic acids. The carbon chain of the organic acid should be between about 4-32 carbon atoms, preferably 8-18 carbons atoms, and most preferably about 8-12 carbon atoms. The linker molecule, therefore, includes the "H" end of the linker, or the organic acid end, and a "T" end, which can be any halogen, organic acid (again), hydroxyl, or amine functionality. The "T" moeity thus supports further cyclization, coupling or displacement reactions whereby the desired Melatonin molecule may be appended to the H/T linker molecule (see FIG. 3, which illustrates attachment of a peptide, but a similar approach may be used to attach Melatonin). For example, deposition of a linker onto reactive oxides present on a calcium aluminate may be conducted by contacting the surface with 12-bromododecanoic acid solution at room temperature (the carboxyl reacts with and bonds to the active oxides on the substrate surface) and then effecting a displacement of the bromine with Melatonin at 4° C. Preferential growth of osteoblasts on CA modified with Melatonin in this way is shown in FIG. 4, where the growth of osteoblasts on the Melatonin modified CA is visibly not only greater than on the unmodified control surface, but the osteoblasts are also growing in a more aggressive, extending fashion (compared to control) typical of good bone cellular interconnectivity. FIGS. 5 and 6 present data corroborating the assertions herein, namely, that Melatonin-modified CA not only foster increased osteoblast growth and proliferation but actually suppress fibroblast formation. Reduced fibroblast formation is associated with reduced scar tissue formation. Data presented in FIGS. 5 and 6 are for the 12-bromododecanoic acid/displacement method, but are believed also to be representative of all Melatonin covalent linkages discussed in this specification. Therefore, a wide variety of H/T chemical (covalent) linkers may be used within the parameters described above. As mentioned in U.S. Published Patent Application No. 20070224678, linkers falling within the above description (although described more narrowly there than herein) may be at least one of an organic acid molecule, a phosphonic acid, an amine, and N,N-dicyclohexylcarbodiimide.

Calcium aluminate compositions may be admixed with water and molded at room temperature. A specific procedure for conducting this admixture is described in detail in Example 1, but those skilled in the art will appreciate that calcium aluminate particles known in the art may be mixed with water to create a paste, which paste will thicken in a few to several minutes (ideally 15-30 minutes) at room temperature to create a relatively thicker paste, which thicker paste can then be molded in any desired three-dimensional form and cured at room temperature overnight, resulting in a hardened ("set") structure. Alternatively, powdered calcium aluminate may be powder deposited as controlled by a computer into a three-dimensional construct which may be wetted and cured at room temperature by carefully spraying finely misted water on the surfaces of the deposited powder and allowing the construct to cure at room temperature.

Functionalization with Melatonin (or its precursors or metabolites) may be accomplished with or without "cell adhesion" peptides. RGD (arg-gly-asp) is the sequence domain that is present in many extracellular matrix proteins, including fibronectin, whose main function is to mediate the adhesion of cells. Studies have shown that this RDG peptide can increase the attachment of mesenchymal stem cells to different substrates (hydroxyapatite, titanium, polymer scaffolds) but does not enhance the spreading of the cells. Cell spreading is important for cell survival and cell differentiation into osteoblasts which are necessary for bone formation and regeneration. For this reason, peptides which bind transmembrane proteoglycans can improve cell attachment and spreading. An example of this latter type of peptide is the KRSR (lys-arg-ser-arg) peptide. KRSR-modified surfaces have also been shown to bind increased numbers of osteoblasts compared to unmodified surfaces and surfaces modified with RGD after four hours of incubation with cells. For all these reasons, it is envisioned that the modification of substrates with Melatonin may also include side-by-side modification of the surfaces with either RGD or KRSR, or preferably with both peptides. By "side-by-side" is meant that some of the reactive surface oxides will include links to peptides whereas other reactive oxides will link to Melatonin or its precursors or metabolites. These modifications may include adsorbing the peptides on the substrate surface, linking them with the same linkers as Melatonin or its precursors or metabolites, or even including the domains within the H/T linker itself or as intermediate distal functionalities to which the Melatonin is further linked at the end of the linker molecule farthest from the substrate surface.

It should be borne in mind that Melatonin-functionalized substrates according to the invention are useful as more than just as bone implants or grafts, but may without limitation be used as scaffolds for tissue engineering, such as is possible by seeding autologous or exogenous kidney, liver or other cells on a scaffold and growing artificial tissue for transplant. The Melatonin-modified calcium aluminate materials of the present invention are preferred for such tissue engineering scaffold use because, except for possibly calcium hexa aluminate which is a calcium aluminate that does not form a hydrate phase, the calcium aluminates are all resorbable and ultimately disappear from the tissue engineered construct for which they thus only temporarily serve as a base. Most or all materials discussed in this specification, therefore, have application in tissue engineering as well as in bone implant and graft applications. The base material may also be calcium phosphate or any inorganic oxide substrate including without limitation aluminates, silicates, zirconates, and zircons (zirconia silicates) because any inorganic oxide substrate will have the reactive groups necessary to perform the organic acid link and melatonin displacement substitution reaction of the preferred embodiment of the invention.

Finally, bone implants or graft materials functionalized with Melatonin according to the present invention may also be coadministered with Platelet Rich Plasma (PRP) for additional improvement of bone healing.

The following EXAMPLES are illustrative.

Example 1

Calcium aluminate (CA) disks were prepared by a room temperature cast of different sized CA aggregates. The aggregates were separated by size during a sifting procedure in which the "cement" (the CA aggregate starting material) was passed through wire screens of different mesh sizes and "caught" on another mesh size. The numbers which follow are all mesh sizes and should be understood to be presented in mesh size units (M). Four different aggregate sizes were used in the casting process −10+30, −30+60, −60 and −325. Five different combinations of the aggregates were cast with compositions of: A: 50 percent −325 and 25 percent each of −30+60 and −60; B: 25 percent of each of the four sizes, C: 33% each of −10+30, −30+60 and −60; D: 50 percent each of −10+30 and −30+60; and E: 100% −10+30. The CA aggregates were dry mixed at room temperature to ensure complete particle distribution. After the dry mixing, double distilled water ("ddH$_2$O") was mixed in an amount adequate (28-38% v/w) to form a slurry (viscosity generally between about 5 and 250 Centipoise) and the cement slurry was allowed to sit undisturbed for 20 minutes at room temperature to thicken to about 200-800 Centipoise. Upon thickening, the cement slurry was poured into a mold and allowed to sit overnight.

Figure 7A:
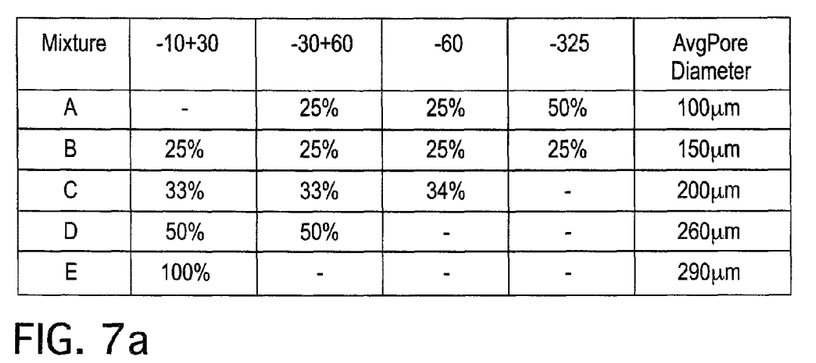
FIGS. 7a-b are a table and a line graph, respectively, identifying data alluded to in Examples below.

The five combinations as molded were removed the following day and each broken into four pieces. The five combinations of the aggregates were thus each exposed to different heat treatments under different conditions, and the pore sizes were subsequently analyzed. The four heat treatment conditions were: room temperature (control); heated to 120° C.; heated to 650° C., and autoclaved at 121° C. with 18 psi of steam. Pore sizes were determined by optical microscopy on a materials microscope (10× magnification; Axioskop2, Zeiss Corp.) and measured using the Axiovision 4 software (Zeiss). A minimum of 100 pores and a maximum of 120 pores were measured for each sample. As shown in FIG. 7a, the average for mixture A was 100 µm, mixture B was 150 µm, mixture C was 210 µm, mixture D was 260 µm, and mixture E was 290 µm. The mixtures containing the larger average pore sizes had not only larger surface pores but also larger interconnecting pores (this is called open porosity as opposed to "closed" porosity) creating a tunnel-like network throughout the material to allow for cell growth into the implant. All samples contained a range of pore sizes from 90 to 350 µm and it was determined that heat treatment (to 1000 degrees Fahrenheit or less) did not affect the average pore diameter of the sample. These results show that CA with a wide range of pore sizes can be cast in order to determine the optimum pore size for cell attachment and proliferation. The mixtures with the two largest pore sizes (260 µm and 290 µm) were determined to be very weak and were deemed unsuitable for further investigation due to lack of mechanical strength.

Figure 7B:
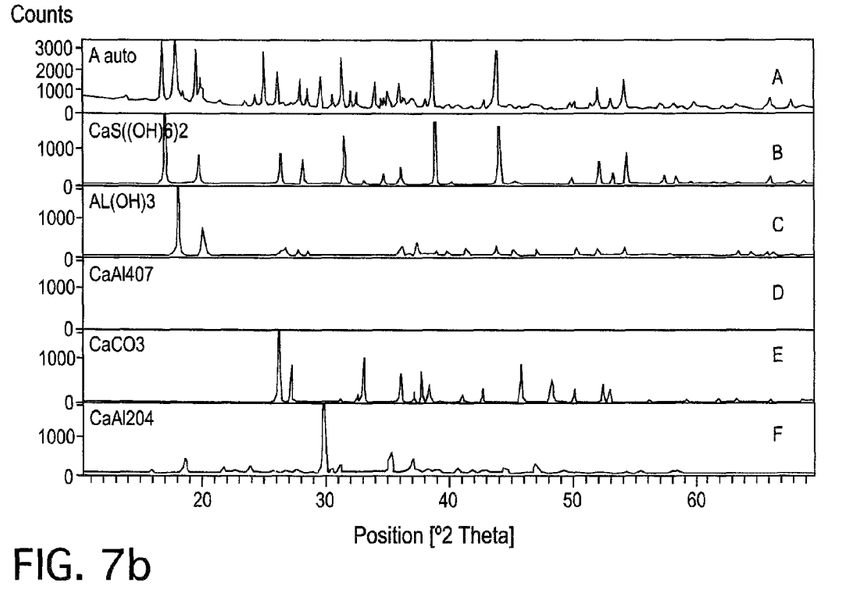

Phase analysis of the above described mixtures was conducted. FIG. 7b shows a PXRD simulated pattern for mixture A autoclaved and reference pattern matches for phases present, with A representing the sample scan and B-F representing scans of Ca$_3$(Al(OH)$_6$)$_2$, Al(OH)$_3$, CaAl$_2$O$_2$, CaCO$_3$ and CaAl$_2$O$_4$, respectively. Although heat treatments did not affect the pore sizes within the materials, they did affect the phases present within the hydrated CA mixtures. Only samples from mixtures A, B and C were then analyzed by powder x-ray diffraction (Panalytical, Xpert Pro) due to their mechanical stability. The samples were scanned from 5 to 70° 2θ with a time per step of 720.090 seconds and a scan speed of 0.008842 degree/minute. Using X'Pert High Score Plus program, the phases present were determined by matching them to spectra in the Powder Diffraction File database. The results are summarized in Table 1. The starting CA aggregates contain the phases, CaAl$_2$O$_4$ and CaAl$_4$O$_2$. These phases are present in all of the mixtures for all heat treatments. All room temperature hydrated samples contained a hydrated phase of CaAl$_2$((OH)$_8$(H$_2$O)$_2$)(H$_2$O)$_{1.84}$ as well as Al(OH)$_3$. In addition, the room temperature mixtures A and B contained Ca$_3$Al$_2$(OH)$_{12}$ and some amounts of Al$_2$O$_3$ the starting material for the aggregates. Mixture C$_{room}$ contained the 3CaO.Al$_2$O$_3$.Ca(OH)$_2$.18H2O phase. In addition, mixtures A$_{120}$, B$_{120}$ and C$_{120}$ all contained Al(OH)$_3$ and (CaO)$_3$Al$_2$O$_3$(H$_2$O)$_6$. The A$_{650}$, B$_{650}$, and C$_{650}$ contained Al(OH)$_3$ and CaCO$_3$ (aggregate starting material) and A$_{650}$ and B$_{650}$ contained an additional 5(CaO)$_3$Al$_2$O$_3$ phase. Finally A$_{auto}$, B$_{auto}$, and C$_{auto}$ contained Al(OH)$_3$, CaCO$_3$ and Ca$_3$(Al(OH)$_6$)$_2$. The phase data are shown in FIG. 2.

Mixture A as heated (only) at room temperature, as prepared in Example 1, was used for all cell and animal testing. Substrates were dipped in a 1 milligram per milliliter solution of Melatonin in ddH$_2$O for 24 hours at 4° C. Excess water was evacuated by placing the samples on a vacuum line for 24 hours (0.1 torr). Infrared reflectance spectra were collected and used to determine whether the Melatonin had adsorbed onto the surface, confirming its presence. The substrate samples were dipped into ddH$_2$O for 15 minutes to rinse and placed back on the vacuum line for 8 hours, followed by a five minute ddH$_2$O rinse and 8 more hours on vacuum line. Melatonin was still present on the surface as confirmed by IR spectral analysis. The amount of Melatonin believed to have adsorbed to the surface was between about one-twentieth to one-sixtieth of a milligram per square millimeter of substrate surface.

Example 2

Melatonin was attached to a calcium aluminate (CA) surface (according to descriptions found elsewhere herein) using a two-step solution deposition dip. First, a quantity of CA disks were placed at room temperature in a 2 mM 12-bromododecanoic acid solution of dry tetrahydrofuran for one hour. The disc substrates were then removed and placed in a 120 degree C. oven for 24 hours. The substrates were then placed in a 1 mg/ml solution of melatonin in methanol with 1 percent pyridine at 4 degrees C. for 24 hours, then dried under vacuum for 24 hours.

The invention claimed is:

1. A bone implant for accelerating bone healing, comprising a solid scaffold containing calcium and a plurality of reactive oxides at the surface thereof having a bone implant surface area, to which surface at least some of the oxide moieties are covalently linked to a linker molecule and melatonin, wherein said melatonin is present in the amount of about one-twentieth to one-sixtieth of a milligram of Melatonin per square millimeter of said bone implant surface area.

2. The bone implant according to claim 1, to which at least some of the oxide moieties are covalently linked a linker molecule and a cell adhesion peptide.

3. The bone implant according to claim 1 wherein said solid scaffold contains porous calcium aluminate having pore sizes between 60-200 micrometers.

* * * * *